US00PP31275P2

(12) United States Plant Patent
Hansen

(10) Patent No.: US PP31,275 P2
(45) Date of Patent: Dec. 24, 2019

(54) **X *MANGAVE* PLANT NAMED 'COFFEE JITTERS'**

(50) Latin Name: **x *Mangave* times *Manfreda longiflora* hybrid**
Varietal Denomination: Coffee Jitters

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/501,031

(22) Filed: Feb. 11, 2019

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
CPC ..... A01H 5/00; A01H 6/12
See application file for complete search history.

*Primary Examiner* — Annette H Para

(57) ABSTRACT

A new and unique x *Mangave* plant named 'Coffee Jitters' characterized by a rounded mound of fleshy, fleshy, linear to lanceolate leaves that develop densely concentrated dark greyed-purple spotting with intense light. The leaves have numerous small, flexible marginal teeth pointing outwardly. The new plant is suitable for the garden or as a potted plant in the garden or home.

1 Drawing Sheet

Botanical classification: x *Mangave* times *Manfreda longiflora* hybrid.
Variety denomination: 'Coffee Jitters'.

STATEMENT REGARDING PRIOR DISCLOSURES UNDER 37 CFR 1.77(b)(6)

The first public disclosure of the claimed plant, in the form of a private sale, was made by Walters Gardens, Inc. on Feb. 12, 2018 to Plant Delights Nursery, Inc. Plants for this sale were obtained from the inventor. No plants of x *Mangave* 'Coffee Jitters' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Coffee Jitters' that was hybridized by the inventor at a wholesale perennial nursery in Zeeland, Mich., USA as a cross between a proprietary unnamed hybrid known as 12-41-2 (not patented) as the female or seed parent times and an unreleased proprietary selection of *Manfreda longiflora* (not patented) as the male or pollen parent. The cross was performed Aug. 12, 2014 and seeds were harvested and sown later the following autumn. Through trials at the same nursery the plant was assigned the breeder code 14-157-6. The new plant has been successfully asexually propagated by sterile shoot-tip tissue culture and by basal offsets at the same nursery in Zeeland, Mich. The asexual propagation has been found to produce stable and identical plants that maintain all the unique characteristics of the original plant.

BRIEF SUMMARY OF THE INVENTION x *Mangave* 'Coffee Jitters' differs from its parents as well as all other *Manfreda, Agave* and x *Mangave* known to the applicant. The female parent is larger in habit, has wider and shorter leaves, and the coloration is more silver-gray with small purple spots, and the marginal teeth are larger and firmer. The *Manfreda longiflora* male parent has thinner, nearly flat leaves, with intermittent coffee and green snake-scale coloration pattern spotting on top with smaller and fewer marginal teeth. The nearest comparison plants are: 'Dreadlocks' U.S. Plant patent application Ser. No. 16/350,480, 'Red Wing' copending U.S. Plant Patent Application, 'Mission to Mars' U.S. Plant Pat. No. 29,393. 'Dreadlocks has more sinuate foliage with mahogany spots on green background. 'Red Wing' has more leaves per plant that are shorter, flatter and more cherry-red colored. 'Mission to Mars' has significantly larger habit, longer and broader foliage that has densely spotted reddish coloration.

'Coffee Jitters' is unique from all of the above cultivars and all *Agave*, x *Mangave* and *Manfreda* known to the inventor by the following combined traits:

1. Flattened mound of linear to lanceolate, deeply channeled, sarcous leaves;
2. Leaves develop dense, dark, coffee-colored overlay filling nearly the entire top side of leaf;
3. Leaf margins have many, small, flexible, outward to recurved, marginal teeth;
4. Moderate to fast growth rate;

BRIEF DESCRIPTION OF THE DRAWING

The photograph of x *Mangave* 'Coffee Jitters' demonstrates the overall appearance of the new plant including the unique traits as two-year-old plants grown in a greenhouse and planted in a full-sun trial garden for the summer in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
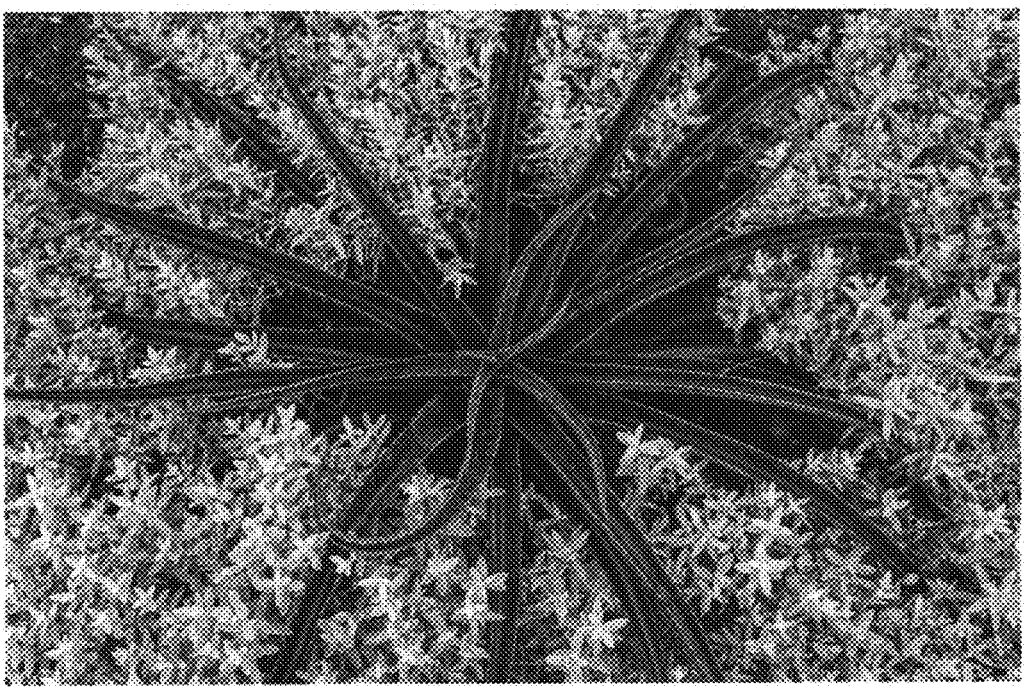
FIG. 1 shows a plant from above.
Figure 2:
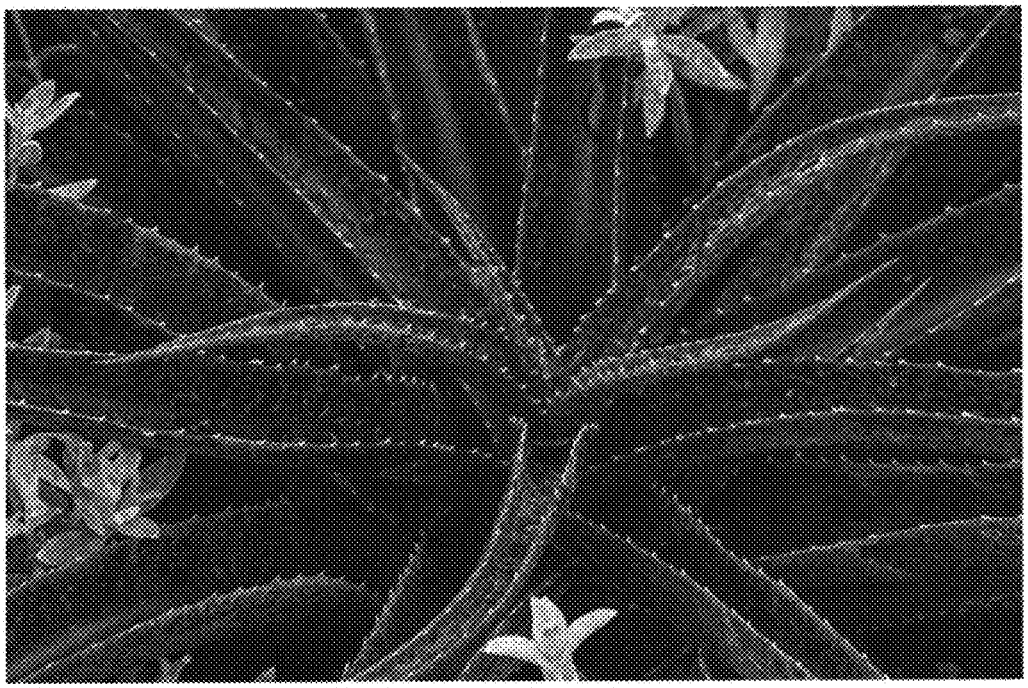
FIG. 2 shows a close-up of the new growth with marginal spines.

The following descriptions and color references are based on the 2015 edition of The Royal Horticultural Society Colour Chart except where common dictionary terms are used. The new plant, x *Mangave* 'Coffee Jitters', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: A proprietary unnamed hybrid known as 12-41-2 as the female or seed patent, and a proprietary selection of *Manfreda longiflora* as the male or pollen parent;

Propagation: By sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS 158B;

Plant shape and habit: Succulent herbaceous perennial with basal rosettes of about 104 leaves radially emerging outwardly from central stem, producing a radially-symmetrical, rounded mound;

Plant size: Foliage height about 32.0 cm tall from soil line to the top of the leaves and about 44.0 cm wide at the widest point just above soil level;

Stem: To about 4.5 cm across; covered with foliage;

Foliage description: Linear to lanceolate; simple; sessile; bi-laterally symmetrical; sarcous; apex narrowly acute without terminal spine; base truncate; older lower leaves slightly concavo-convex and younger upper leaves flat; margins flat; margins serrate with small, flexible, outwardly pointing teeth; glabrous abaxial and adaxial; slightly lustrous abaxial and adaxial;

Terminal spine size: Absent;

Marginal teeth size: About 1.0 mm long and 1.0 mm wide at base, average spacing about 4.5 mm apart;

Leaf size: To about 36.0 cm long, about 34.0 mm wide toward middle; center base about 8.0 mm thick at basal midrib; older leaves channeled to about 10.0 mm deep, younger leaves nearly flat; average about 32.0 cm long, 29.0 mm wide and 6.0 mm thick in longitudinal center; spots on both adaxial and abaxial vary from 2.0 mm diameter to nearly solid greyed-purple with intense light;

Foliage fragrance: None observed;

Leaf number: About 104 per plant before flowering;

Leaf blade color:

*Adaxial* (*low light*).—Nearest RHS 139A with spots blend between RHS 187B and RHS N187B.

*Abaxial* (*low light*).—Variable with nearest RHS 137A mottled with nearest RHS 138B.

*Adaxial* (*high light*).—Mottled with patches nearest RHS 187A and nearest RHS N187B with younger foliage showing mottling of nearest RHS 146C.

*Abaxial* (*high light*).—Variably mottled with patches nearest RHS N186C and RHS 146B toward stem, distally mottled with patches nearest RHS N187B and blend between RHS 187B and RHS 186A.

*Teeth*.—Nearest RHS 155B with slight blush at base nearest RHS 187C.

*Terminal spine*.—Not present.

Petiole: Leaves sessile;

Veins: Parallel; not distinct abaxial or adaxial;

Flower description: Not yet observed;

Fruit and seed not observed;

Disease resistance: x *Mangave* 'Coffee Jitters' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Coffee Jitters' as herein described and illustrated.

* * * * *